(12) United States Patent
Kuntze et al.

(10) Patent No.: US 6,620,276 B1
(45) Date of Patent: Sep. 16, 2003

(54) APPARATUS FOR TRANSPORTING A CONTINUOUS WEB, AND FOR MANIPULATING THE WEB

(75) Inventors: Lothar Kuntze, Rheinbach (DE); Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/744,277

(22) PCT Filed: Jul. 16, 1999

(86) PCT No.: PCT/US99/16138
§ 371 (c)(1),
(2), (4) Date: Feb. 13, 2001

(87) PCT Pub. No.: WO00/04855
PCT Pub. Date: Feb. 3, 2000

(30) Foreign Application Priority Data

Jul. 22, 1998 (EP) .............................................. 98113667

(51) Int. Cl.⁷ ............................................. B32B 31/08
(52) U.S. Cl. ...................... 156/164; 156/229; 156/302; 156/494; 156/516
(58) Field of Search ................................. 156/164, 302, 156/494, 495, 516, 519, 552, 163, 229, 160, 161

(56) References Cited

U.S. PATENT DOCUMENTS

| 4,081,301 A | | 3/1978 | Buell | 156/164 |
|---|---|---|---|---|
| 4,227,952 A | * | 10/1980 | Sabee | 156/164 |
| 4,488,923 A | | 12/1984 | Pieniak | 156/199 |
| 4,578,133 A | * | 3/1986 | Oshefsky et al. | 156/164 |
| 4,610,751 A | | 9/1986 | Eschler | 156/517 |
| 4,726,876 A | * | 2/1988 | Tomsovic, Jr. | 156/552 |
| 5,091,039 A | * | 2/1992 | Ujimoto et al. | 156/164 |
| 5,665,191 A | * | 9/1997 | Johansson et al. | 156/161 |
| 5,716,478 A | * | 2/1998 | Boothe et al. | 156/242 |

FOREIGN PATENT DOCUMENTS

EP 0 451 705 A1 10/1991 ........... A61F/13/15

OTHER PUBLICATIONS

International Search Report for PCT/US99/16138 mailed Sep. 14, 1999.

* cited by examiner

Primary Examiner—Jeff H. Aftergut
Assistant Examiner—John L. Goff
(74) Attorney, Agent, or Firm—Michael P. Hayden; Michael S. Kolodesh; Ken K. Patel

(57) ABSTRACT

The object of the invention is achieved by an apparatus (10) comprising a plurality of means for forming web loops (101), each means for forming web loops being positioned between adjacent web support plates (20), wherein each of the web support surfaces lies in an arc, the arcs lying around the circumference of a circular path, and wherein the web support surfaces and means for forming web loops (101) are rotatably mounted about the axis of the circular path. In a prefered embodiment of the invention, the means for forming web loops (101) is provided by rotatably driving the web support plates (20) around the circular path with a circumferential velocity, wherein the circumferential velocity is varied between a minimum circumferential velocity and a maximum circumferential velocity so that the distance between adjacent web support plates (20) varies between a minimum distance and a maximum distance. Preferably the circumferential velocity of the web support plates (20) varies according to a sinusoidal function, and wherein one cycle of the sinusoidal function corresponds to one complete rotation of the web support plate (20) around the circular path. The invention also relates to a process for transporting a continuous web around the apparatus whereby the distance between adjacent web support plates (20) is greater than the minimum distance, and wherein the web is transported around the circular path so that a web loop (101) is formed when the distance between adjacent web support plates (20) decreases towards the minimum distance.

9 Claims, 5 Drawing Sheets

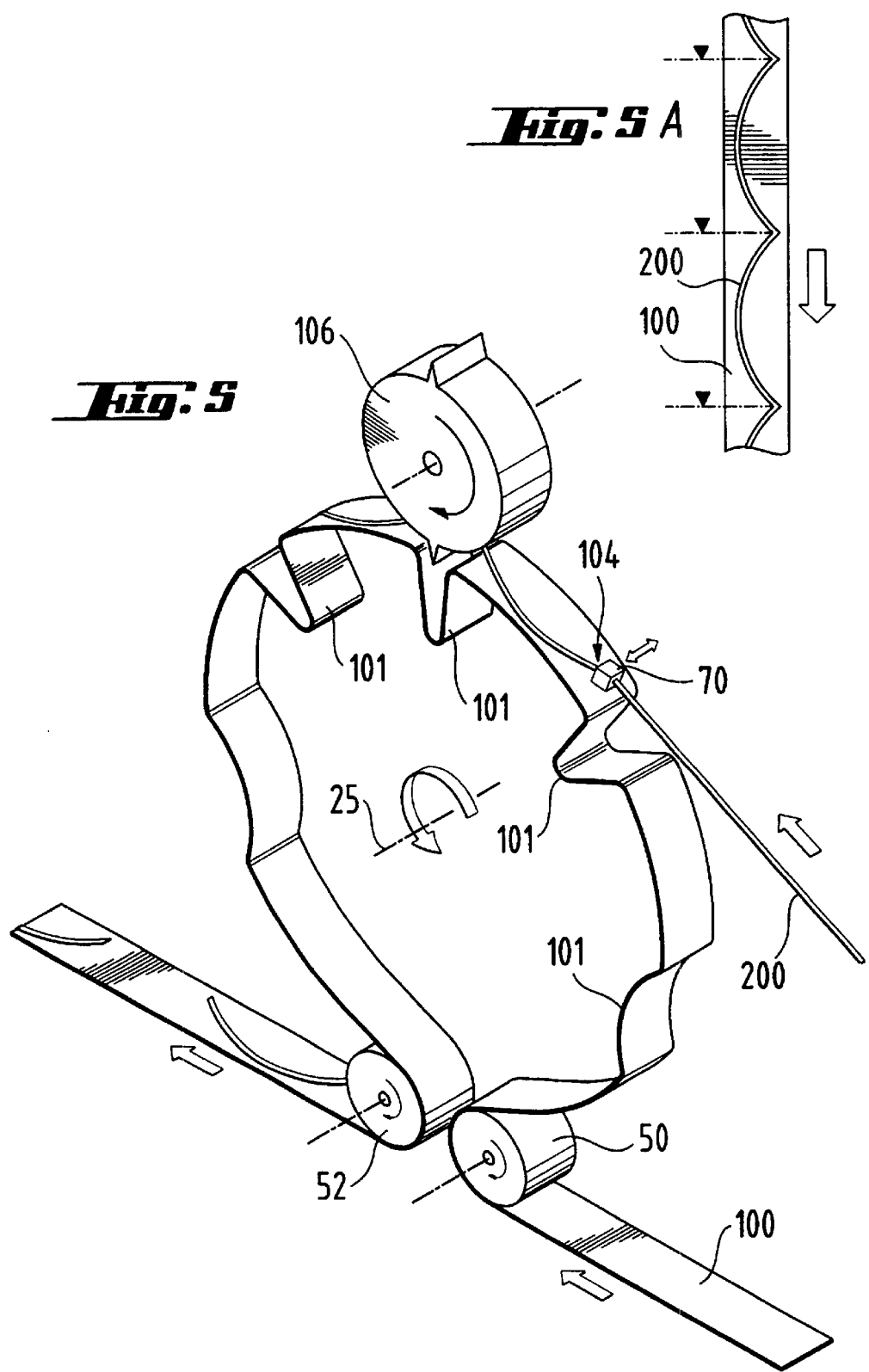

APPARATUS FOR TRANSPORTING A CONTINUOUS WEB, AND FOR MANIPULATING THE WEB

The present invention relates to an apparatus for transporting a continuous web, and for manipulating the web especially to form web loops. The apparatus is particularly useful in the manufacture of disposable absorbent articles, including diapers, adult incontinence products, sanitary napkins and the like.

Manufacturing processes are often required to provide discrete strips of a material onto a continuous web, in such a way that the discrete webs of material are spaced apart along the length of the continuous web. Features manufactured in this way include elastic strips, one example of which is the elastic leg cuffs applied to diapers.

U.S. Pat. No. 4,081,301, issued on March 1978, discloses a process for applying a material, such as an elastic material, to a continuous web. The material is only glued along the length of the web in discrete sections, so that when the web is cut the elastic material remains extended only in the discrete section in which it has been glued, and contracts elsewhere.

U.S. Pat. No. 4,227,952, issued on Oct. 14$^{th}$ 1980, discloses a conveyor which carries spaced web support plates and wherein a continuous web is tucked in between the support plates to form web loops is known. Various features, such as leg elastic, are then applied to the web which lies on the web support plate, but not to the web loop. This forming process requires less elastic material and provides material savings.

An apparatus of this type comprises a plurality of web support plates, each web support plate having an outer web support surface. However the apparatus is mechanically complex and not well-suited to high speed manufacturing machines.

The object of the present invention is to provide a mechanically simpler and more reliable apparatus for applying features, including elastic features, to a continuous web, in particular on a high speed manufacturing machine.

A further object of the invention is to provide a process for transporting and manipulating a web using the apparatus of the invention.

SUMMARY OF THE INVENTION

The object of the invention is achieved by an apparatus comprising a plurality of means for forming web loops, each means for forming web loops being positioned between adjacent web support plates, wherein each of the web support surfaces lies in an arc, the arcs lying around the circumference of a circular path, and wherein the web support surfaces and means for forming web loops are rotatably mounted about the axis of the circular path. In a preferred embodiment of the invention, the means for forming web loops is provided by rotatably driving the web support plates around the circular path with a circumferential velocity, wherein the circumferential velocity is varied between a minimum circumferential velocity and a maximum circumferential velocity so that the distance between adjacent web support plates varies between a minimum distance and a maximum distance. Preferably the circumferential velocity of the web support plates varies according to a sinusoidal function, and wherein one cycle of the sinusoidal function corresponds to one complete rotation of the web support plate around the circular path.

The invention also relates to a process for transporting a continuous web around the apparatus whereby the distance between adjacent web support plates is greater than the minimum distance, and wherein the web is transported around the circular path so that a web loop is formed when the distance between adjacent web support plates decreases towards the minimum distance.

BRIED DESCRIPTION OF THE DRAWINGS

FIG. 5 shows a representation in perspective of the path of a continuous web as it passes around the apparatus of the present invention in a third embodiment of the process of the invention. FIG. 5$a$ shows the profile of a curved elastic feature applied to the continuous web.

DETAILED DESCRIPTION OF THE INVENTION

It will be readily apparent to those skilled in the art that although the following description of the present invention is in connection with a single use diaper structure having discrete elastic regions or strips, the present invention may be practiced with equal facility on nearly any web.

In the following description a "continuous web" is a web of material which is continuous in the machine direction. A preferred continuous web comprises a plurality of interconnected single use disposable absorbent articles, such as diapers. Typically, each diaper is comprised of an absorbent pad element or absorbent core, and elastomeric elements or patches. The absorbent pad elements and the elastomeric elements are located between a backsheet and a topsheet, or alternatively, on top of a backsheet or topsheet. The continuous webs of backsheet material and topsheet material are preferably maintained under very slight tension in the machine direction to prevent wrinkling and to facilitate registration with the diaper assembly and converting operations until the completed diaper web is severed into discrete diapers by cutting across the width of the web.

Figure 1:
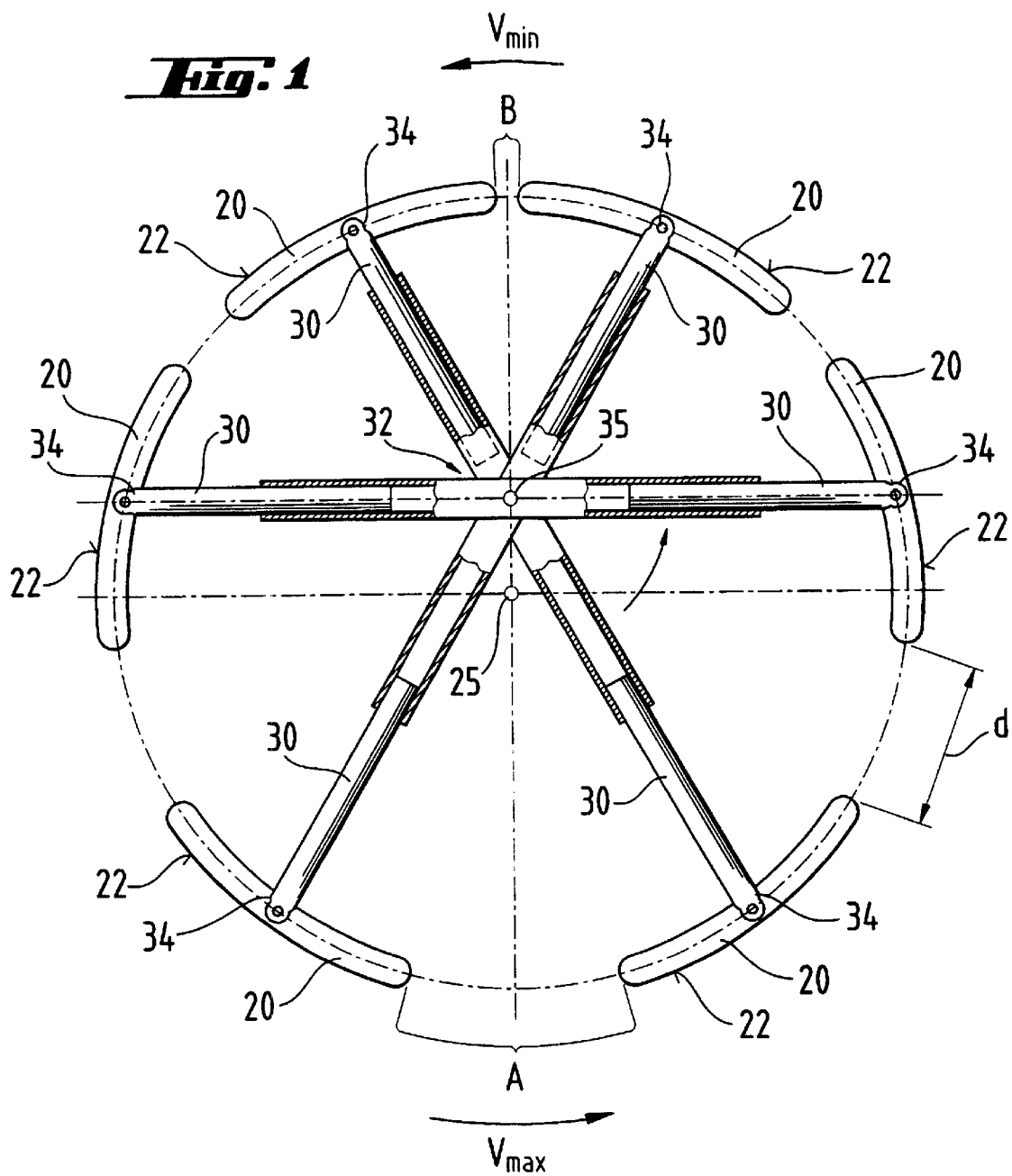
FIG. 1 shows a diagrammatic representation of a cross-section through the apparatus of the present invention.
Figure 2:
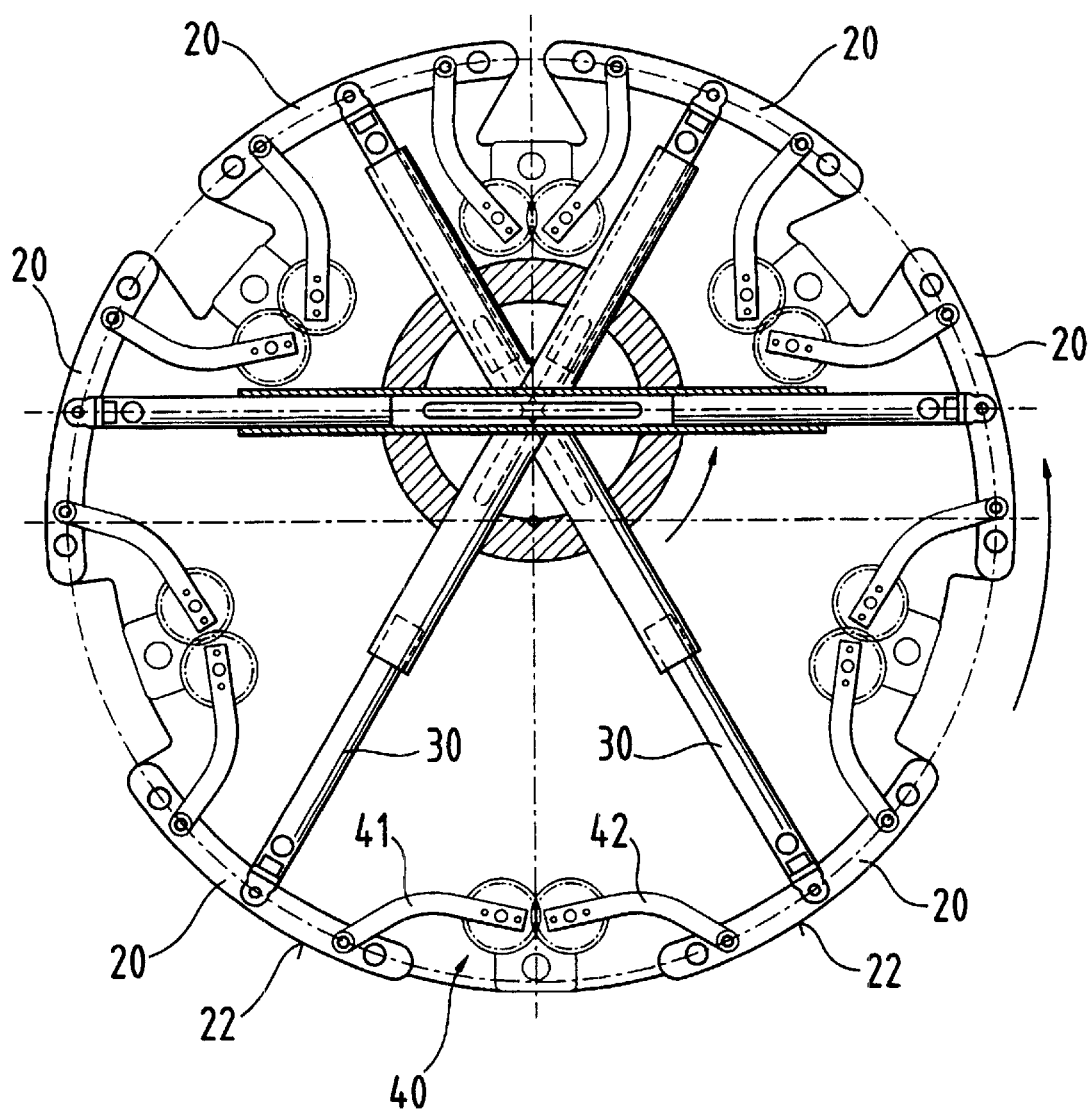
FIG. 2 shows a more detailed cross-section through the apparatus of the present invention, including linkages between adjacent web support plates.

FIG. 1 and 2 illustrate a cross-section through a preferred embodiment of the apparatus of the present invention. An apparatus having six web support plates 20 is illustrated, each web support plate comprises a web support surface 22 facing outwardly, and the web support plates 20 are rotated so that the web support surfaces 22 trace out an essentially circular path. The apparatus will now be described with reference to one of the web support plates as it moves around the circular path illustrated in FIG. 1. An anti-clockwise rotation is illustrated, but the invention could be equally well put into practice with a clockwise rotation. As the web support plate 20 passes through point A of the circular path (at the bottom of the circular path as illustrated in FIG. 1), it has a maximum circumferential velocity $V_{max}$. As the web support plate 20 is rotated towards the top of the circular path it is decelerated until it reaches a minimum circumferential velocity $V_{min}$ at point B of the circular path. As the web support plate 20 continues around the circular path it speeds up until it returns to point A. Adjacent web support plates are spaced apart by a distance d. The adjacent web support plates either side of point A in FIG. 1 have a maximum distance d between them. As the web support plates are rotated one of the web support plates has a faster circumferential velocity than the adjacent web support plate, and the faster web support plate catches up with the slower web support plate, thereby reducing the distance d between them. When the adjacent web support plates lie either side of point B in FIG. 1 the distance between them is a minimum. It is preferred that the circumferential velocity V of the web support plates 20 varies according to a sinusoidal function, and wherein one cycle of the sinusoidal function corresponds to one complete rotation of the web support plate 20 around the circular path.

Consequently a continuous web 100 placed against the web support plates is transported around the apparatus and furthermore the continuous web 100 is manipulated in such a way that a web loop 101 is formed between adjacent web support plates 20 as the adjacent web support plates 20 move closer together.

In a particularly preferred embodiment of the invention the circumferential velocity of the web support plates is controlled by mechanical means. In FIG. 1 the mechanical means comprises six extendible arms 30, that is to say one extendible arm 30 to drive each of the web support plates 20. Each extendible arm 30 has a proximal end 32 and a distal end 34, the proximal end 32 of each extendible arm 30 being mounted on a second axis of rotation 35 and the distal end 34 of each extendible arm 30 being pivotally mounted on each web support plate 20. The principal axis 25 and the second axis 35 are parallel but off-set in relation to each other, so that the extendible arms 30 drive the web support plates 20 around the circular path with the variable circumferential velocity.

FIG. 2 shows a similar schematic representation to FIG. 1, and additionally FIG. 2 also illustrates preferred linking means 40. Adjacent web support plates 20 are pivotally connected to each other by linking means 40. The linking means illustrated comprise a first link 41 and a second link 42. The first link 41 and the second link 42 are pivotally connected to each other near one end of the links, the other end of each link being pivotally connected near to the ends of adjacent web support plates 20.

Figure 3:
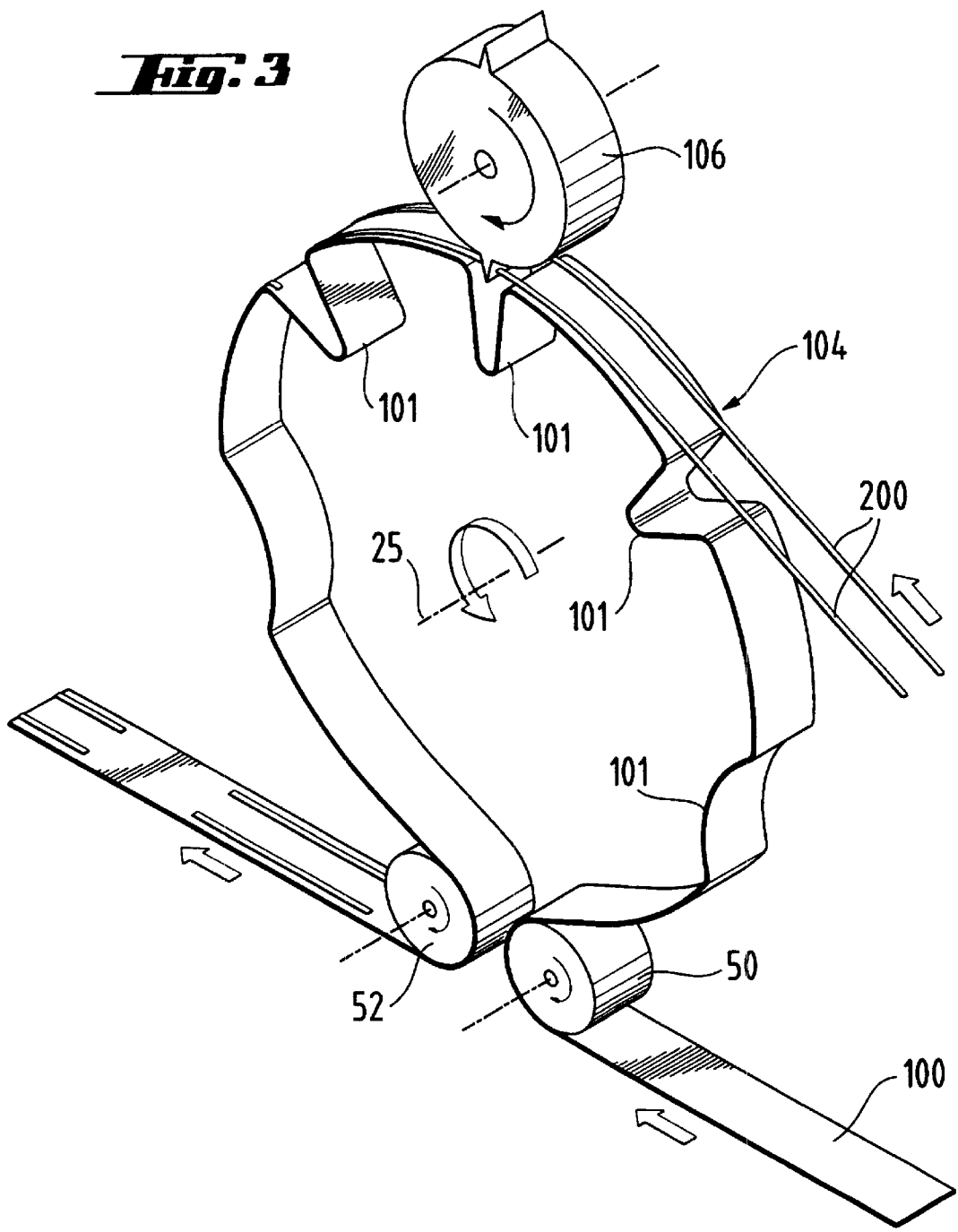
FIG. 3 shows a representation in perspective of the path of a continuous web as it passes around the apparatus of the present invention in a first embodiment of the process of the invention.

FIG. 3 illustrates the path of a continuous web 100 as it passes around the apparatus of the present invention in a first embodiment of the process of the invention. The web is fed to a transfer roll 50 by a feeding means (not shown) and is transferred to the web support surface of the apparatus. The apparatus itself is not shown in FIG. 3 for clarity. As the web is drawn around the circular path by means of the web support plates (not shown), web loops 101 are formed as described hereinabove. FIG. 3 also shows a pair of elastic strips 200 being fed by a feeding means (not shown) to application points 104. At the application points 104 the elastic strips 200 are attached to the continuous web 100. The means of attachment is not important in this invention and may be achieved by glue, hot melt, self-adhesive material or any other means. FIG. 3 also shows a cutting station 106 at which the elastic strips 200 are cut into discrete strips. The continuous web 100 is not necessarily cut at the cutting station 106, indeed it is preferred that the continuous web 100 is not cut on the apparatus of the present invention. The continuous web 100 is not cut because the cutting station 106 is adjacent to a web loop 101 as shown. Subsequently the web 100 accelerates around the apparatus, thereby releasing the web loops 101, and the continuous web with discrete lengths of elastic material adhered to it, the discrete lengths of elastic material being spaced apart, is peeled off the web support surface at a second transfer roll 52.

Figure 4:
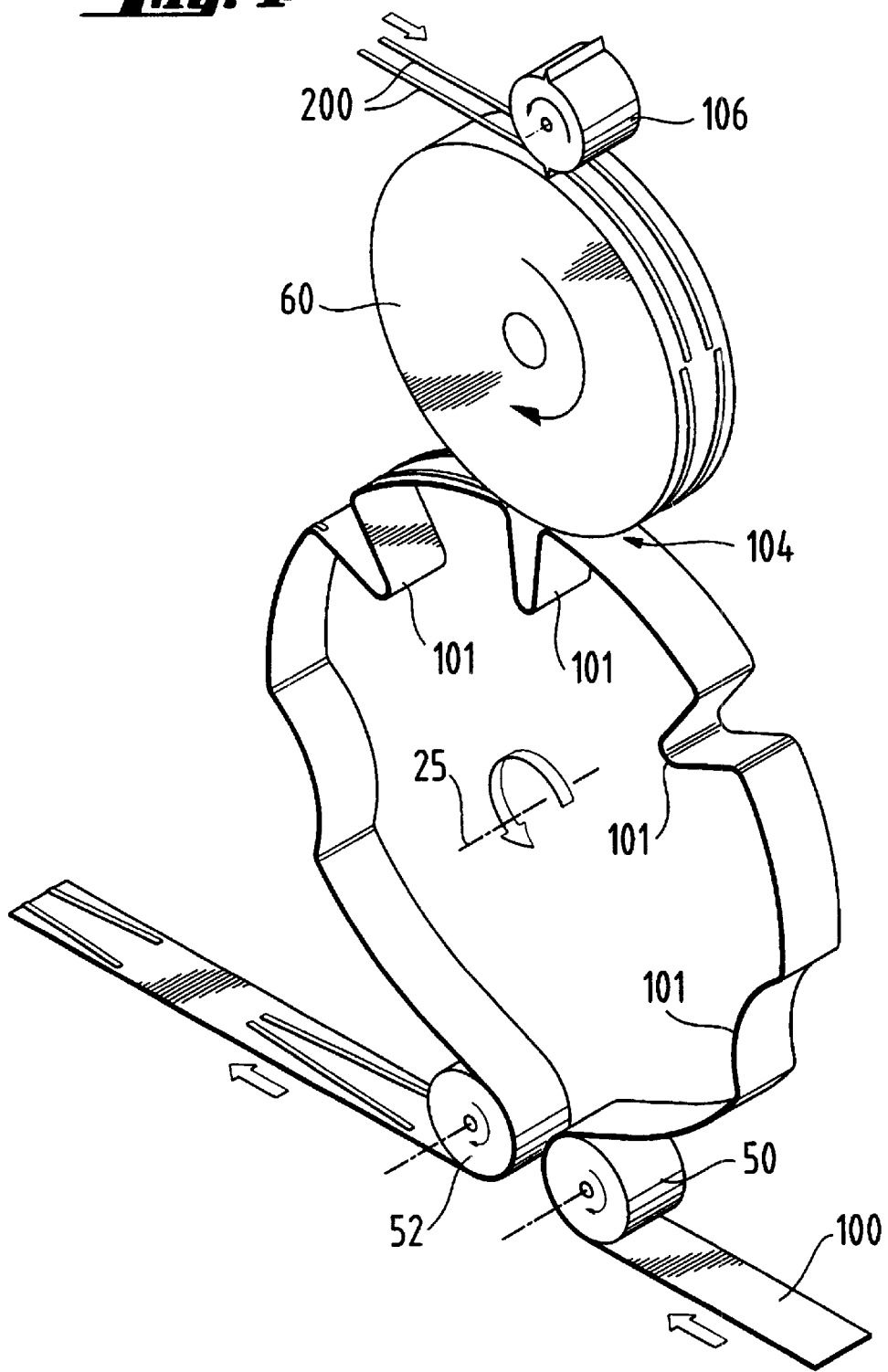
FIG. 4 shows a representation in perspective of the path of a continuous web as it passes around the apparatus of the present invention in a second embodiment of the process of the invention.

FIG. 4 illustrates the path of a continuous web 100 as it passes around the apparatus of the present invention in a second embodiment of the process of the invention. The web is fed to a transfer roll 50 by a feeding means (not shown) and is transferred to the web support surface of the apparatus. The apparatus itself is not shown in FIG. 4 for clarity. As the web is drawn around the circular path by means of the web support plates (not shown), web loops 101 are formed as described hereinabove.

In FIG. 4 the elastic strips 200 are provided on the surface of an applicator roll 60. The elastic strips 200 are cut and deflected on the surface of the applicator roll 60 prior to the application point 104.

FIG. 5 illustrates the path of a continuous web 100 as it passes around the apparatus of the present invention in a third embodiment of the process of the invention. The web is fed to a transfer roll 50 by a feeding means (not shown) and is transferred to the web support surface of the apparatus. The apparatus itself is not shown in FIG. 5 for clarity. As the web is drawn around the circular path by means of the web support plates (not shown), web loops 101 are formed as described hereinabove.

In FIG. 5 a deflection means 70 is provided in order to apply an elastic strip 200 in a curved profile. The deflection means 70 is adjacent to the application point 104 and moves in the cross-machine direction with a frequency corresponding to the speed of the cycle of the web support plates 20.

FIG. 5*a* shows the profile of a curved elastic feature applied to the continuous web.

What is claimed is:

1. An apparatus for transporting and manipulating a continuous web to form a loop in the web, comprising:

a plurality of adjacent web support plates movable along a circular path centered on a principal axis, each web support plate having a convexly arcuate outer web support surface describing an arc segment of the circular path and being circumferentially spaced from each following web support plate, each web support plate being pivotally linked to each adjacent web support plate by linking means; and means for driving each web support plate around the circular path at a variable circumferential velocity such that the web support plate and the following web support plate move alternately circumferentially closer together and circumferentially farther apart during each revolution of the web support plate around the circular path.

2. The apparatus of claim 1 wherein the circumferential velocity varies according to a sinusoidal function having a period equal to the revolution of the web support plate around the circular path.

3. The apparatus of claim 1 wherein the driving means comprises an extendible arm having an outer end pivotally attached to the web support plate and an inner end disposed at an axis of rotation offset from the principal axis.

4. The apparatus of claim 1 comprising means for feeding a strip onto a portion of the web on the web support surface and means for severing the strip into discrete segments.

5. A process for transporting and manipulating a continuous web to form a loop in the web, comprising the steps of:

placing successive spaced portions of the web on adjacent web support plates moving along a circular path centered on a principal axis, each web support pate having a convexly arcuate outer web support surface describing a segment of the circular path and being circumferentially spaced from each following web support plate,;

driving each web support plate to transport the spaced portions of the web around the circular path at a variable circumferential velocity such that the web support plate and the following web support plate move circumferentially closer together and thereby form the loop in a portion of the web between the space portions; and applying a strip at an application point adjacent to the circular path such that the strip is applied to only the portions of the web on the web support plates and not to the portion of the web forming the loop.

6. The process of claim 5 comprising the step of severing the strip between the web support plates such that the strip remains attached to only the portions of the web on the web support plates and not to the portion of the web forming the loop.

7. The process of claim 5 wherein the strip is elastic and is applied under tension.

8. A process for transporting and manipulating a continuous web to form a loop in the web, comprising the steps of:

placing successive spaced portions of the web on adjacent web support plates moving along a circular path centered on a principal axis, each web support plate having a convexly arcuate outer web support surface describing a segment of the circular path and being circumferentially spaced from each following web support plate;

driving each web support plate to transport the spaced portions of the web around the circular path at a variable circumferential velocity such that the web support plate and the following web support plate move circumferentially closer together and thereby form the loot in a portion of the web between the spaced portions; and severing a strip into discrete strip segments and applying the strip segments at an application point adjacent to the circular path such that the strip segments are applied to only the portions of the web on the web support plates and not to the portion of the web forming the loop.

9. The process of claim 8 wherein the strip is elastic and the strip segments are applied under tension.

\* \* \* \* \*

UNITED STATES PATENT AND TRADEMARK OFFICE
CERTIFICATE OF CORRECTION

PATENT NO. : 6,620,276 B1
DATED : September 16, 2003
INVENTOR(S) : Lothar Kuntze et al.

It is certified that error appears in the above-identified patent and that said Letters Patent is hereby corrected as shown below:

Column 2,
Line 7, delete "BRIED" and insert therefor -- BRIEF --.

Column 5,
Line 11, delete "space portions" and insert therefor -- spaced portions --.

Column 6,
Line 14, delete "loot" and insert therefor -- loop --.

Signed and Sealed this

Twentieth Day of July, 2004

JON W. DUDAS
*Acting Director of the United States Patent and Trademark Office*